United States Patent
Liu et al.

(10) Patent No.: US 8,648,218 B2
(45) Date of Patent: Feb. 11, 2014

(54) METHOD FOR PREPARING PHENOLIC COMPOUNDS

(71) Applicant: Industrial Technology Research Institute, Hsinchu (TW)

(72) Inventors: Chiung-Fang Liu, Taipei (TW); Chih-Ching Chen, New Taipei (TW); Chih-Hao Chen, Hsinchu (TW); Pei-Jung Yu, Pingzhen (TW); Ying-Hsi Chang, Zhongli (TW); Hou-Peng Wan, Guishan Township (TW); Hom-Ti Lee, Zhubei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/683,473

(22) Filed: Nov. 21, 2012

(65) Prior Publication Data

US 2013/0150630 A1    Jun. 13, 2013

(30) Foreign Application Priority Data

Dec. 13, 2011 (TW) .............................. 100145895 A

(51) Int. Cl.
*C07C 37/00* (2006.01)
*C07C 37/54* (2006.01)
*G10G 1/00* (2006.01)
*C10L 5/00* (2006.01)

(52) U.S. Cl.
USPC ............. 568/799; 585/242; 585/319; 44/605; 568/750; 530/503

(58) Field of Classification Search
None
See application file for complete search history.

(56) References Cited

U.S. PATENT DOCUMENTS

| | | | | |
|---|---|---|---|---|
| 2,666,077 | A * | 1/1954 | McGrath ...................... | 518/717 |
| 4,605,790 | A | 8/1986 | Wojtkowski | |
| 5,959,167 | A | 9/1999 | Shabtai et al. | |
| 6,172,272 | B1 | 1/2001 | Shabtai et al. | |
| 6,207,808 | B1 | 3/2001 | Naae et al. | |
| 7,964,761 | B2 | 6/2011 | Zmierczak et al. | |
| 2003/0115792 | A1 | 6/2003 | Shabtai et al. | |
| 2004/0115736 | A1 | 6/2004 | Kozak | |
| 2007/0015947 | A1 | 1/2007 | Marker | |
| 2008/0050792 | A1 * | 2/2008 | Zmierczak et al. ........... | 435/161 |
| 2012/0012035 | A1 | 1/2012 | Blank et al. | |

FOREIGN PATENT DOCUMENTS

| | | |
|---|---|---|
| CN | 1583695 A | 2/2005 |
| CN | 1264985 C | 7/2006 |
| CN | 101768052 A | 7/2010 |
| CN | 102173980 A | 9/2011 |
| GB | 743592 A | 1/1956 |
| GB | 759811 A | 10/1956 |
| JP | 2004-137347 A | 5/2004 |
| JP | 2006-086979 A | 3/2006 |
| JP | 2008-024880 A | 2/2008 |
| TW | 201114907 A1 | 5/2011 |
| WO | WO 2010/106182 A1 | 9/2010 |

OTHER PUBLICATIONS

Taiwan Office Action for Appl. No. 100145895 dated Sep. 3, 2013.
Bu et al., "Phenol and phenolics from lignocellulosic biomass by catalytic microwave pyrolysis," Bioresource Technology, 2011, vol. 102, pp. 7004-7007.
Bui et al., "Hydrodeoxygenation of guaiacol Part II: Support effect for CoMoS catalysts on HDO activity and selectivity," Applied Catalysis B: Environmental, 2011, vol. 101, pp. 246-255.
Bui et al., "Hydrodeoxygenation of guaiacol with CoMo catalysts. Part I: Promoting effect of cobalt on HDO selectivity and activity," Applied Catalysis B: Environmental, 2011, vol. 101, pp. 239-245.
Elliott et al., "Catalytic Hydroprocessing of Chemical Models for Bio-oil," Energy & Fuels, 2009, vol. 23, pp. 631-637.
Mochizuki et al., "Deoxygenation of Bio-oil over Reduced Catalysts," Journal of the Japan Petroleum Institute, 2011, vol. 54, No. 3, pp. 222-223.
Nenkova et al., "Production of Phenol Compounds by Alkaline Treatment of Technical Hydrolysis Lignin and Wood Biomass," Chemistry of Natural Compounds, 2008, vol. 44, No. 2, pp. 182-185.
Nimmanwudipong et al., "Catalytic Conversion of Guaiacol Catalyzed by Platinum Supported on Alumina: Reaction Network Including Hydrodeoxygenation Reactions," Energy Fuels, 2011, vol. 25, pp. 3417-3427.
Park et al., "Catalytic decomposition of benzyl phenyl ether to aromatics over cesium-exchanged heteropolyacid catalyst," Korean J. Chem. Eng., 2011, vol. 28, No. 5, pp. 1177-1180.

* cited by examiner

*Primary Examiner* — Johann R Richter
*Assistant Examiner* — Mark Luderer
(74) *Attorney, Agent, or Firm* — Birch, Stewart, Kolasch & Birch, LLP

(57) ABSTRACT

In an embodiment of the disclosure, a method for preparing a phenolic compound is provided. The method includes providing a lignin depolymerization product, and hydrogenating the lignin depolymerization product under iron oxide and hydrogen gas to prepare a phenolic compound. The prepared phenolic compound is a crude phenolic composition including phenol, methylphenol, dimethylphenol or a combination thereof.

8 Claims, No Drawings

METHOD FOR PREPARING PHENOLIC COMPOUNDS

CROSS REFERENCE TO RELATED APPLICATIONS

This Application claims priority of Taiwan Patent Application No. 100145895, filed on Dec. 13, 2011, the entirety of which is incorporated by reference herein.

BACKGROUND

1. Technical Field

The technical field relates to a method for preparing a phenolic compound from lignin depolymerization products.

2. Description of the Related Art

Currently, the main source of phenol is crude oil. Crude oil is distillated though an atmospheric tower to form light oil. Light oil is hydrogenated and re-fractionated to form benzene. Benzene is sulfonated, melted and treated by halogenated aromatic alkali to form phenol. Phenol is an important chemical raw material which is capable of making dyes, drugs, phenolic resin and adhesive, etc. Due to limited petrochemical resources, phenol is in short supply every year, for example, there was a shortfall of the global supply of phenol in the amount of 534,000 tonnes in 2011, therefore finding an alternate source of materials and manufacturing technology other than petrochemical phenol is an important task.

The lignin of biomass mainly comprises carbon (C), hydrogen (H) and oxygen (O). Lignin is depolymerized to form phenolic compounds such as 4-methoxyphenol ($C_7H_8O_2$), o-methoxyphenol (guaiacol, $C_7H_8O_2$) or 2,6-dimethoxyphenol (syringol, $C_8H_{10}O_3$). High-priced phenol (NT$60/kg) or crude phenol (NT$40/kg, a mixture of phenol, methylphenol and dimethylphenol) is acquired in removing the methoxy group of benzene of lignin depolymerization product. Using biomass as a substitute for petrochemical phenol raw materials, which reduces the dependence on petrochemical phenol and helps to enhance the total value of biomass, is a technology with a great source of materials and development potential.

SUMMARY

One embodiment of the disclosure provides a method for preparing a phenolic compound comprising: providing a lignin depolymerization product, and hydrogenating the lignin depolymerization product under iron oxide and hydrogen gas to prepare a phenolic compound.

A detailed description is given in the following embodiments.

DETAILED DESCRIPTION

In the following detailed description, for purposes of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One embodiment of the disclosure provides a method for preparing a phenolic compound, comprising the following steps: A lignin depolymerization product is provided. The lignin depolymerization product is then hydrogenated under iron oxide and hydrogen gas to prepare a phenolic compound.

The lignin depolymerization product is obtained by depolymerization of lignin through, for example, a hydrolysis, pyrolysis, hydrothermal, liquefaction or ion solution method and may comprise 4-methoxyphenol

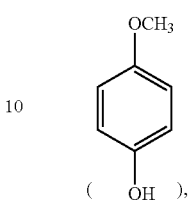

o-methoxyphenol

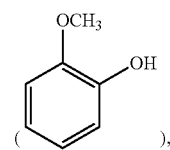

2,6-dimethoxyphenol

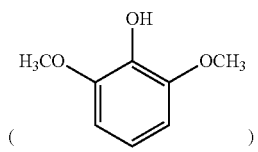

or a combination thereof.

The iron oxide serving as a catalyst may be triiron tetraoxide ($Fe_3O_4$) with a particle size equal to or less than about 5 nm and a specific heat equal to or less than about 7 J/g·° C.

The lignin depolymerization product is hydrogenated at a temperature of about 160-360° C., at a pressure of hydrogen gas of about 5-100 atm and at a space velocity of about 10-60 $h^{-1}$.

The prepared phenolic compound is a crude phenolic composition which may comprise phenol, methylphenol (cresol), dimethylphenol (xylenol) or a combination thereof.

In the disclosure, the catalyst powder of triiron tetraoxide ($Fe_3O_4$) with a specific heat equal to or less than 7 J/g·° C. and a particle size equal to or less than 5 μm is utilized in the hydrogenation/deoxygenation of the lignin depolymerization products to prepare the phenolic compounds. The catalyst, a good conductor of heat, with the characteristics of low specific heat, small particle size and large contact area with reactants facilitates the breaking of the carbon-oxygen (C—O) bond of benzene to accelerate the formation of phenol. In the present hydrogen gas system, the breaking of the carbon-oxygen (C—O) bond of benzene is an endothermic reaction. Nevertheless, the hydrogenation of the benzene free radical after the breaking is an exothermic reaction. Thus, the main reaction includes hydrocracking and hydrogenation and produces phenol (>80%). The side reaction includes the electrophilic substitution reaction and produces o-methylphenol (<10%) and m-methylphenol (<10%). Therefore, in the disclosure, the production of phenol is highly selective. The substances (including FeO and $Fe_2O_3$) constituting the catalyst are the two substances which can reach a heat balance each other under the certain temperature, hydrogen gas and water vapor. The catalyst carries the energy which the hydrocracking needs to effectively break the carbon-oxygen bond. Under hydrogen gas, the free radical formed by the breaking of the carbon-oxygen (C—O) bond is hydrogenated with the hydrogen gas. This reaction is an exothermic reaction and the emitted energy is immediately absorbed and brought away by the catalyst. For example, in the hydrogenation of o-methoxyphenol, a series of endothermic and exothermic reactions are thermodynamically regulated through the catalyst to prevent the overheating or an extremely low temperature of the reaction system caused by the conventional catalyst with poor heat conductivity due to the problem of energy transfer causing reaction termination or more side reactions. Besides, after hydrogenation, the product and the catalyst can easily be separated through a simple magnetic separation method due to the returned magnetism of $Fe_3O_4$.

EXAMPLE 1

Preparation of the Catalyst ($Fe_3O_4$)

First, $FeCl_3$ and $FeCl_2$ were mixed with a molar ratio of 2:1 and added to a 100 mL beaker to prepare an acidic solution. Next, a concentrated ammonia solution was slowly dropped into the acidic solution until a black precipitate was formed. After the precipitation was completed, an underlying precipitate was collected and washed by deionized water several times. The precipitate was then dried in an oven at 105° C. to prepare the catalyst ($Fe_3O_4$).

In accordance with XRD analysis, the characteristic peaks of the catalyst ($Fe_3O_4$) prepared by this example were $2\theta=30.16°, 35.7°, 43.33°, 53.6°, 57.1°$ and $62.8°$ which corresponded respectively to the crystal surfaces of (220), (311), (400), (422), (511) and (440) of cubic form of $Fe_3O_4$. The above-mentioned characteristic peaks corresponded to the standard peaks of $Fe_3O_4$. Thus, the catalyst prepared by this example was indeed $Fe_3O_4$ in accordance with the analytic results of XRD.

EXAMPLE 2

Preparation, Conversion Rate and Qualitative Analysis of the Phenol

First, 0.335 g o-methoxyphenol (guaiacol, $C_7H_8O_2$) was blended with 6.365 g n-tetradecane ($C_{14}H_{30}$) to prepare a feed (guaiacol:n-tetradecane=5%:95%). The feed and the catalyst were filled into a tube with a set weight hourly space velocity (WHSV). The tube was then placed in a columnar rapid-screening reaction tube. The valves of the reaction tube were closed. Next, hydrogen gas was filled into the reaction tube to a required pressure. The pressure of the reaction tube was released after sustaining pressure for a period of time. The pressure sustaining and leakage tests for the reaction tube were performed. The above procedure was repeated three times. Next, the columnar rapid-screening reaction tube was placed in a furnace which was preheated to a reaction temperature. The temperature was detected by a K-type thermocouple. The furnace had four ports for insertion of the reaction tube and swung with a frequency of 30 Hz. The experimental time of the production of phenol from the lignin depolymerization product was set to one hour. In this example, three kinds of catalyst were utilized in the production of phenol. The first was the catalyst with hydrogenation pretreatment. The second was the catalyst with vulcanization pretreatment. The third was the catalyst without pretreatment. In the hydrogenation pretreatment, the catalyst was hydrogenated at 160° C., 240° C. and 360° C., respectively, for 15 hours under 100% hydrogen gas. In the vulcanization pretreatment, the catalyst was vulcanized at 160° C., 240° C. and 360° C., respectively, for 15 hours under 5% hydrogen gas and 95% hydrogen sulfide ($H_2S$). In this example, the set reaction conditions of the production of phenol included a reaction temperature of 280° C., a pressure of hydrogen gas of 50 atm (25° C.), a space velocity of $10\ h^{-1}$ and a reaction time of one hour.

After the above-mentioned experiment was completed, the liquid product was measured by a GC-FID (GC-FID, column, HP-1; cross-linked methyl siloxane; 25 m £ 0.32 mm £ 0.17 μm)(the alteration of the temperature gradient was set as follows: 40° C. (retaining 10 minutes)→50° C. (heating rate: 2° C./min)→70° C. (heating rate: 1° C./min)→100° C. (heating rate: 3° C./min)→110° C. (heating rate: 1° C./min)→300° C. (heating rate: 10° C./min)(retaining 1 minute)) to calculate the conversion rate of the o-methoxyphenol (guaiacol, $C_7H_8O_2$). The results are shown in Table 1. The manner of calculation was described as follows:

Conversion rate=[(the weight percent of the o-methoxyphenol in the reactant−the weight percent of the o-methoxyphenol in the product)/the weight percent of the o-methoxyphenol in the reactant]× 100%

TABLE 1

| Catalysts | Pretreatment temperature (° C.) | Conversion rate (%) |
|---|---|---|
| Hydrogenation pretreatment | 160 | 100 |
|  | 240 | 76.4932 |
|  | 360 | 48.9548 |
| Vulcanization pretreatment | 160 | 96.51316 |
|  | 240 | 100 |
|  | 360 | 99.94 |
| No pretreatment | — | 100 |

In this example, when the catalyst with vulcanization pretreatment was utilized, the conversion rate of the o-methoxyphenol was greater than 96%, almost complete conversion. When the catalyst with hydrogenation pretreatment was utilized, the conversion rate of the o-methoxyphenol was apparently affected by the pretreatment temperature, as the pretreatment temperature increased and the conversion rate thereof decreased. When the pretreatment temperature was 160° C., the conversion rate thereof was 100%. However, when the pretreatment temperature was raised to 360° C., the conversion rate thereof decreased to 49% only. This is because $Fe_2O_3$ was reduced to FeO in the catalyst under hydrogen gas and caused a loss of catalytic activity. When the catalyst without pretreatment was utilized, the conversion rate of the o-methoxyphenol was 100%. Compared to the commercial catalysts with pretreatment, the present catalyst without pretreatment also possessed activity, substantially lowering the cost.

The composition of the liquid product was then analyzed by a GC-MS (GC-MSD; HP 5973; column, HP-1; cross-linked methyl siloxane, 25 m×0.32 mm×0.17 μm)(the alteration of the temperature gradient was set as follows: 40° C. (retaining 10 minutes)→300° C. (heating rate: 5° C./min) (retaining 10 minutes)).

In accordance with the analytic results of GC-MS, regardless of use of the catalyst with hydrogenation pretreatment, the catalyst with vulcanization pretreatment or the catalyst without pretreatment in the production of phenol, the obtained main product was phenol.

EXAMPLE 3

The Affection of Catalyst Pretreatment on Selectivity of Products (Using o-methoxyphenol as a Reactant)

In this example, the catalysts with various pretreatments were utilized. The selectivity of the production of phenol from the o-methoxyphenol was analyzed by a GC-FID. The analytic results were described as follows. When the catalyst with hydrogenation pretreatment was utilized, in the liquid product, the selectivity of phenol was about 60%. The selectivity of o-cresol and m-cresol was about 10% each. Thus, the selectivity of crude phenol (including phenol, o-cresol and m-cresol) was greater than 80%. The other product was cyclohexanone (less than 20%), also being a high-priced chemical raw material (NT$60/kg).

When the catalyst with vulcanization pretreatment was utilized, in the liquid product, the selectivity of phenol was about 50%. However, only a small amount of o-cresol and m-cresol was obtained. The fully deoxy products such as cyclohexane (NT$42/kg) and cyclohexene (NT$49/kg), also being high-priced chemical raw materials, were about 45%.

EXAMPLE 4

The Affection of Reaction Time on Selectivity of Products (Using o-methoxyphenol as a Reactant)

In this example, the reaction time was set to 0.5, 1 and 2 hours, respectively. The experimental results were described as follows. When the reaction time was 0.5 hour, the selectivity of crude phenol was 100%, wherein phenol was 60% and the rest was o-cresol and m-cresol. When the reaction time was 1 hour, the selectivity of crude phenol was about 85%, and the rest was cyclohexanone. When the reaction time was 2 hours, the selectivity of crude phenol was about 82%. In this product, cyclohexene was also obtained in addition to cyclohexanone. Therefore, the o-methoxyphenol was first formed into phenol and other phenolic compounds via a hydrocracking reaction. As the reaction time was increased, the cyclohexanone was formed by the continuous hydrogenation reaction and de-olefin. Next, the cyclohexene was further formed by hydrodeoxygenation. Thus, to this example, when the reaction time was set to 0.5 hour, the phenolic compounds with high yield were immediately obtained. However, as the reaction time was prolonged, other hydrogenated by-products were generated instead.

EXAMPLE 5

The Affection of Reaction Pressure on Selectivity of Products (Using o-methoxyphenol as a Reactant)

In this example, when the reaction pressure was set to 5-25 atm, in the liquid product, the selectivity of crude phenol was 100%. However, when the reaction pressure was raised to 50 atm, 15% cyclohexanone was formed and the rest was crude phenol. Therefore, the o-methoxyphenol was successfully converted into crude phenol under a $Fe_3O_4$ catalyst and the pressure of hydrogen gas of 5 atm. However, when the reaction pressure was raised to 50 atm, some crude phenol was further hydrogenated and deoxygenated which caused a low yield of crude phenol. Thus, when $Fe_3O_4$ was utilized as a catalyst, the highest conversion rate of crude phenol was obtained at which only 5 atm of pressure of hydrogen gas was required.

EXAMPLE 6

The Affection of Reaction Temperature on Selectivity of Products (Using o-methoxyphenol as a Reactant)

In this example, the reaction temperature was set to 240° C., 280° C. and 320° C., respectively. The experimental results were described as follows. When the reaction temperature was 240° C., the selectivity of crude phenol was 100%. However, the increased reaction temperature caused hydrogenation of crude phenol to form cyclohexanone, cyclohexene and even cyclohexane. Thus, in order to produce crude phenol with a high yield, the reaction temperature was set to 240° C. An increase in the reaction temperature caused a low yield of crude phenol.

EXAMPLE 7

The Selectivity of Products from Hydrogenation of Various Lignin Depolymerization Products

In this example, (1) a mixture of 5% o-methoxyphenol and 95% n-tetradecane, (2) a mixture of 5% 2,6-dimethoxyphenol and 95% n-tetradecane, (3) a mixture of 5% 4-methoxyphenol and 95% n-tetradecane and (4) a mixture of 1.85% o-methoxyphenol, 3.15% 2,6-dimethoxyphenol and 95% n-tetradecane were selected as various reactants in the experiment of selectivity of products from hydrogenation. The experimental results were described as follows. When 2,6-dimethoxyphenol and 4-methoxyphenol were respectively utilized as a reactant in the hydrogenation/deoxygenation, in this product, the selectivity of crude phenol was 100%. That is, $Fe_3O_4$ catalyst possessed high efficiency of conversion of crude phenol from other lignin depolymerization products. When the mixture of 1.85% o-methoxyphenol, 3.15% 2,6-dimethoxyphenol and 95% n-tetradecane was utilized as a reactant, the product was still crude phenol. Therefore, $Fe_3O_4$ catalyst possessed a high efficiency of converting crude phenol from various lignin depolymerization products.

It will be apparent to those skilled in the art that various modifications and variations can be made to the disclosed embodiments. It is intended that the specification and examples be considered as exemplary only, with a true scope of the disclosure being indicated by the following claims and their equivalents.

What is claimed is:

1. A method for preparing a phenolic compound, comprising: providing a lignin depolymerization product; and hydrogenating the lignin depolymerization product under iron oxide and hydrogen gas to prepare a phenolic compound, wherein the iron oxide consists of Fe3O4.

2. The method for preparing a phenolic compound as claimed in claim 1, wherein the lignin depolymerization product comprises 4-methoxyphenol

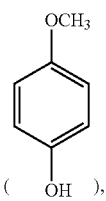

o-methoxyphenol

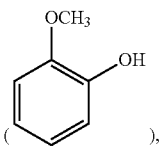

2,6-dimethoxyphenol

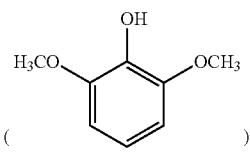 [SMILES: COc1cccc(OC)c1O]

or a combination thereof.

3. The method for preparing a phenolic compound as claimed in claim 1, wherein the iron oxide has a particle size equal to or less than 5 μm.

4. The method for preparing a phenolic compound as claimed in claim 1, wherein the lignin depolymerization product is hydrogenated at a temperature of 160-360° C.

5. The method for preparing a phenolic compound as claimed in claim 1, wherein the lignin depolymerization product is hydrogenated at a pressure of hydrogen gas of 5-100 atm.

6. The method for preparing a phenolic compound as claimed in claim 1, wherein the lignin depolymerization product is hydrogenated at a space velocity of 10-60 $h^{-1}$.

7. The method for preparing a phenolic compound as claimed in claim 1, wherein the phenolic compound is a crude phenolic composition.

8. The method for preparing a phenolic compound as claimed in claim 7, wherein the crude phenolic composition comprises phenol, methylphenol, dimethylphenol or a combination thereof.

* * * * *